United States Patent
Houben et al.

(10) Patent No.: US 11,950,992 B2
(45) Date of Patent: Apr. 9, 2024

(54) ON-THE-GO PACKAGE OF ABSORBENT ARTICLES AND METHOD OF MAKING

(71) Applicants: ONTEX BV, Buggenhout (BE); ONTEX GROUP NV, Erembodegem (BE)

(72) Inventors: Annemie Houben, Ghent (BE); Herman Vandevelde, Aalter (BE); Eva Staelens, Eeklo (BE)

(73) Assignees: ONTEX BV, Buggenhout (BE); ONTEX GROUP NV, Erembodegem (BE)

( * ) Notice: Subject to any disclaimer, the term of this patent is extended or adjusted under 35 U.S.C. 154(b) by 139 days.

(21) Appl. No.: 17/425,014

(22) PCT Filed: Jan. 23, 2020

(86) PCT No.: PCT/EP2020/051596
§ 371 (c)(1),
(2) Date: Jul. 22, 2021

(87) PCT Pub. No.: WO2020/152256
PCT Pub. Date: Jul. 30, 2020

(65) Prior Publication Data
US 2022/0079819 A1 Mar. 17, 2022

(30) Foreign Application Priority Data
Jan. 24, 2019 (EP) ..................................... 19153563

(51) Int. Cl.
*A61B 17/06* (2006.01)
*A61F 13/15* (2006.01)
(Continued)

(52) U.S. Cl.
CPC .. *A61F 13/55145* (2013.01); *A61F 13/15747* (2013.01); *A61F 13/5611* (2013.01);
(Continued)

(58) Field of Classification Search
CPC ..... B65D 71/00; B65D 71/063; B65B 11/004; B65B 35/50; B65B 63/04;
(Continued)

(56) References Cited

U.S. PATENT DOCUMENTS 4,059,220 A * 11/1977 Lorenz ..................... B65D 5/22
229/199
4,460,088 A * 7/1984 Rugenstein ........ B65D 75/5838
229/87.05
(Continued)

FOREIGN PATENT DOCUMENTS

CA 2025856 A1 3/1991
EP 0357000 A1 * 3/1990
(Continued)

OTHER PUBLICATIONS

International Search Report and Written Opinion for PCT/EP2020/051596, dated Feb. 21, 2020.

*Primary Examiner* — Luan K Bui
(74) *Attorney, Agent, or Firm* — VIVICAR Law, PLLC (57) ABSTRACT

A substantially cuboid reclosable flexible package (8) for transporting multiple personal hygiene absorbent articles "on-the-go" is disclosed. It has a front wall (81), a rear wall (82), two opposed side walls (83,83) and two opposed end walls (84,84'). It includes a stack of at least two personal hygiene absorbent articles (1,100) comprising a garment attachment adhesive covered by a removable release paper (2), and which are folded inwardly with the removable release paper (2) exposed. The folded absorbent articles are free of an individual wrapping pouch and comprise closure means (7) for securing said folding. The package (8) is made of a plastic or paper wrap sealed at one position on either the front (81), the rear (82), or one of the two side walls (83,83'), and on the two end walls (84,84'). It comprises, on at least (Continued)

Fig.8a one wall, a tear-open flap (86) limited by at least one tearing line (87).

17 Claims, 4 Drawing Sheets

(51) Int. Cl.
*A61F 13/551* (2006.01)
*A61F 13/56* (2006.01)
*B65B 11/00* (2006.01)
*B65B 35/50* (2006.01)
*B65B 63/04* (2006.01)
*B65D 71/06* (2006.01)

(52) U.S. Cl.
CPC ............ *B65B 11/004* (2013.01); *B65B 35/50* (2013.01); *B65B 63/04* (2013.01); *B65D 71/063* (2013.01)

(58) Field of Classification Search
CPC .......... A61F 13/55145; A61F 13/15747; A61F 13/5611; A61F 13/5511
USPC .............. 206/440, 441; 604/385.03, 385.04, 604/385.05; 53/443, 447, 467
See application file for complete search history.

(56) References Cited

U.S. PATENT DOCUMENTS

| | | | | |
|---|---|---|---|---|
| 5,413,568 | A | * | 5/1995 | Roach ................. A61F 13/5514 604/389 |
| 5,484,636 | A | * | 1/1996 | Berg, Jr. ............. A61F 13/5514 604/389 |
| 5,569,228 | A | * | 10/1996 | Byrd ................... A61F 13/5514 604/389 |
| 5,860,588 | A | * | 1/1999 | Anchor ................. B65D 5/067 229/184 |
| 6,923,321 | B2 | * | 8/2005 | Samolinski ........... A61F 15/001 604/385.04 |
| 7,100,769 | B2 | * | 9/2006 | Tourre ............... B65D 75/5833 206/233 |
| 7,789,291 | B2 | * | 9/2010 | Andersson ........ B65D 75/5833 383/207 |
| 8,052,664 | B2 | * | 11/2011 | Shimizu .............. A61F 13/5515 604/385.03 |
| 2017/0000666 | A1 | | 1/2017 | Stephens |

FOREIGN PATENT DOCUMENTS

| | | |
|---|---|---|
| EP | 0419770 A1 | 4/1991 |
| EP | 0930052 A1 | 7/1999 |
| EP | 3323395 A4 | 5/2018 |
| WO | 9925285 A1 | 5/1999 |
| WO | 0139708 A2 | 6/2001 |

* cited by examiner

ON-THE-GO PACKAGE OF ABSORBENT ARTICLES AND METHOD OF MAKING

CROSS-REFERENCE TO RELATED APPLICATIONS

This application is the national stage application of corresponding international application number PCT/EP2020/051596, filed Jan. 23, 2020, which claims priority to and the benefit of European application no. 19153563.2, filed Jan. 24, 2019, which is hereby incorporated by reference in its entirety.

TECHNICAL FIELD

The present invention relates to absorbent articles such as sanitary napkins, pantyliners and incontinence pads. More particularly, the present invention relates to a packaging allowing to easily transport multiple absorbent articles of this type, at once, in a sanitary manner.

BACKGROUND

Absorbent articles such as sanitary napkins, pantyliners and incontinence pads are devices that are typically worn in the crotch region of an undergarment. More specifically, sanitary napkins and pantyliners are worn by women in a pair of panties that is normally positioned between the wearer's legs, adjacent to the perineum area. Sanitary napkins and pantyliners are designed to absorb and retain body fluids or discharges (e.g., urine and menses) from the body of women and to prevent body and clothing from soiling. A wide variety of shapes and dimensions of sanitary napkins and pantyliners is currently used by women for the collection of body fluids. Similarly, incontinence pads are worn in the undergarment of both women and men who have light to medium incontinence problems, to absorb and retain urine.

In the past, these disposable absorbent articles were essentially packaged in a box or bag from which the consumer withdrew the ready-to-use articles as needed. When the consumer needed only one article for later use, the consumer had to take precautions to protect the article from soiling or contamination from the time it was removed from the box or bag until the article was used. For example, if a woman wanted to carry a sanitary napkin with her for use away from home, she had to take precautions to ensure that the article was not damaged or soiled when carried in her purse or pocket.

The problem of protecting the disposable absorbent article once it is removed from the package in which it is sold has been addressed in the prior art and individually packaged disposable absorbent articles are now well known in the art. Feminine sanitary napkins, pantyliners, as well as incontinence pads, are now often sold in such an "on-the-go" configuration. Commercially available products of this range are commonly folded in three overlapping sections along the length of the product ("tri-folded") and such tri-folded product is arranged in a sealed pouch (typically made from oil-based materials e.g. polyethylene film) to thereby maintain the product folded and sanitary prior to use. Such configuration has the advantage of being generally discreet: the size of the folded product allows it to be held in the hand, and the pouch is generally provided with graphics and colours to hide the product it encloses.

Absorbent products of this type conventionally include an adhesive arranged on a garment facing side of the product ("garment attachment adhesive") to enable the user to attach the product to an undergarment during use. Prior to use, the garment attachment adhesive is covered by a removable release paper that is intended to protect the adhesive and prevent the garment attachment adhesive from adhering to the pouch prior to use. Alternatively, the release paper may by omitted, and the interior surface of the pouch may include a non-stick coating (e.g. silicone) to prevent the garment attachment adhesive from adhering to the pouch. When ready for use, a user opens the pouch, unfolds the pouch and product, removes the absorbent product from the pouch, removes the release paper (if such paper is employed) and attaches the product to the undergarment.

Users, and also manufacturers, are however more and more concerned about the environmental impact of having each product in a single use pouch, in particular for products like pantyliners which can be used on a daily basis. There is thus a need for ready-to-use products that can be carried, preferably discreetly, in a purse or pocket and still remain sanitary, whilst using less packaging, and in particular less plastics. And there is a need to provide also a cheap and effective process that allows such product differentiation to be achieved.

SUMMARY OF THE INVENTION

In a first aspect, the present disclosure relates to a substantially cuboid reclosable flexible package of personal hygiene absorbent articles, having a front wall, a rear wall, two opposed side walls and two opposed end walls, wherein the package includes a stack of at least two personal hygiene absorbent articles comprising a garment attachment adhesive covered by a removable release paper, and which are folded inwardly with the removable release paper exposed, characterised in that the folded absorbent articles are free of an individual wrapping pouch and comprise closure means for securing said folding and characterised in that the package is made of a wrapping material sealed at one position on either the front, the rear, or one of the two side walls, and on the two end walls, and in that it comprises, on at least one wall, a tear-open flap limited by at least one tearing line.

In a further aspect, the present disclosure relates to a process for making a substantially cuboid reclosable flexible package of personal hygiene absorbent articles free of an individual wrapping pouch, having a front wall, a rear wall, two opposed side walls and two opposed end walls, comprising the steps of:
(i) providing personal hygiene absorbent articles comprising a garment attachment adhesive covered by a removable release paper;
(ii) folding inwardly each individual absorbent article into a folded article wherein the removable release paper is exposed;
(iii) providing each folded article with closure means for securing said folding;
(iv) stacking at least two folded articles;
(v) wrapping a wrapping material around the resulting stack of folded articles;
(vi) sealing the wrapping material at one position on either the front, the rear, or one of the two side walls, and on the two end walls;
(vii) providing at least one wall of the package with a tear-open flap limited by at least one tearing line.

The product of the present invention overcomes the problems of prior art products, as it provides an "on-the-go" solution which uses less plastics (in particular no individual pouches), which is discreet (package similar to a tissue pack, which everyone can have in his purse or pocket), and which keeps the product hygienic (reclosable package). Although such kind of packages has been known for decades in the field of handkerchiefs for example, and although the concern about overuse of plastics and willingness to decrease its usage has appeared already years ago, to the best of applicant's knowledge, such a solution has never been described, and even less commercialized, and is thus unique and obviously not straightforward.

Whilst implementing such solution, applicant has further been faced to various difficulties for which no readily apparent solutions were available in his usual work and technological environment. The present invention for example has the advantage of avoiding that the folded product opens again (i.e. unfolds) before being enclosed in the package, thereby avoiding problems at the stacking step and on the conveyor belt of the manufacturing line, whilst in prior art products, the individual wrapping pouch itself served to maintain the product folded. As a further example the present invention has the advantage of improving the manufacturing line speed whilst avoiding the use of premade bags which in most cases in the prior art, created a bottleneck along the manufacturing line.

The present invention has the additional advantage of reducing the total cost of raw material used to provide the final product to the consumer. Not including an individual pouch, but still offering an "on-the-go" product results in a significant cost reduction.

Other objects and advantages of this invention will become apparent hereinafter.

DETAILED DESCRIPTION OF THE INVENTION

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein. Herein, "comprise" and "include" mean that other elements and/or other steps which do not affect the end result can be added. Each of these terms encompasses the terms "consisting of" and "consisting essentially of".

"Centreline" as used herein means an imaginary line that is equidistant from lateral surfaces of the element referred to, typically running through said element such to divide said element into two substantially equal halves.

The recitation of numerical ranges by endpoints includes all numbers and fractions subsumed within that range, as well as the recited endpoints.

The expression "absorbent article" or "personal hygiene articles" or "personal hygiene absorbent articles" refers to articles which absorb and contain body exudates or discharges such as body fluids, and is intended to include articles worn in the crotch region of a garment like sanitary napkins, pantyliners and incontinence pads.

The expression "disposable" refers to articles which are intended to be discarded after a single use, composted, or otherwise disposed of in an environmentally compatible manner. (That is, they are not intended to be laundered or otherwise restored or reused as an absorbent article.)

The expressions "sanitary napkin" and "pantyliners" refer to articles which are worn by females adjacent to the pudendal region which are intended to absorb and contain the various exudates which are discharged from the body (e.g., blood, menses, and urine).

The expression "body surface" refers to surfaces of absorbent articles and/or their component members which face the body of the wearer, while the term "garment surface" refers to the opposite surfaces of the absorbent articles and/or their component members that face away from the wearer when the absorbent articles are worn. Absorbent articles and components thereof, including the topsheet, backsheet, absorbent core, and any individual layers of their components, have a body surface and a garment surface.

The expression "wrapping material", "wrap" and "wrapping" refer to a generally sheet-like, soft, flexible material used to cover or enclose something, like paper- or plastic-based sheet or film.

Personal hygiene absorbent articles suitable for use herein are typically of the disposable type and are preferably either female personal hygiene articles such as sanitary napkins and pantyliners, or incontinence pads, for use by women or men.

Disposable absorbent articles for use according to the present invention typically comprise a liquid impermeable backsheet having a garment facing side and a body facing side opposite thereto, a liquid permeable topsheet positioned on the body facing side of the backsheet, and an absorbent core positioned between the backsheet and the topsheet. The absorbent core may comprise cellulosic fibres and/or super absorbent polymer particles, and may further comprise a nonwoven wrap that encloses said fibres and/or particles therein. A further optional intermediate layer may be comprised between the topsheet and the core, and can be selected from any nonwoven typically used in the art of acquisition and distribution layers, such as air-through-bonded nonwovens.

The absorbent articles further comprise one or more adhesive regions on the garment facing side of the backsheet that typically extend along the length of the absorbent article. Said one or more regions are herein grouped under the designation "garment attachment adhesive". Said adhesive is adapted to adhere to a garment surface of the underwear of the wearer, during use of the article. Rubber-based and hotmelt polyolefin adhesives, for example, are commonly used for this purpose. Preferably a strip of longitudinally oriented adhesive provides good protection against either the front or the back of the sanitary napkin being detached from the wearer's undergarment. The strip may be continuous or intermittent; it may be straight or have a swirl pattern. More than one longitudinally oriented strip may be used, for example 2, 3, 4 or 5, or the adhesive region may cover the full width of the article. Transversally oriented stripes or patterns of adhesive may also be used.

The absorbent articles further include a, preferably single piece of, release paper covering at least the attachment adhesive. It may be substantially of the same size and shape as the absorbent article (thereby facilitating a die-cut operation during manufacture). This release paper is removed for attaching the absorbent article to the underwear. The expression "release paper" refers to any sheet material used to protect the adhesive element from contamination prior to use and to prevent the attachment adhesive from adhering to any third surface prior to use. The release paper may be made of kraft paper, calendered paper, or other materials as are well known in the art without departing from the spirit and scope of the present invention. A particularly preferred release paper is made of machine glazed or machine finished paper having a basis weight of about 35 to 38 gsm, preferably about 36 gsm. The face of the paper oriented towards the attachment adhesive may be coated with a release coating such as silicone. Paper has the advantage of being made from a natural resource which is renewable and recyclable. The release paper may be partially transparent or opaque, coloured throughout the mass or by printing; it may be partially printed with different kinds of graphics, using one or more colours. It may comprise an indication to the user (e.g. a graphic indicating the orientation of the product when in use, letters indicating the size of the product).

The absorbent articles of the invention are folded such that the release paper provides protection for the article when it is inwardly folded and the release paper is exposed. Preferably, the release paper and the absorbent product are folded together around two fold lines to provide a folded article. Alternatively, the number of fold lines can be one or three.

Figures 1, 2, 3:
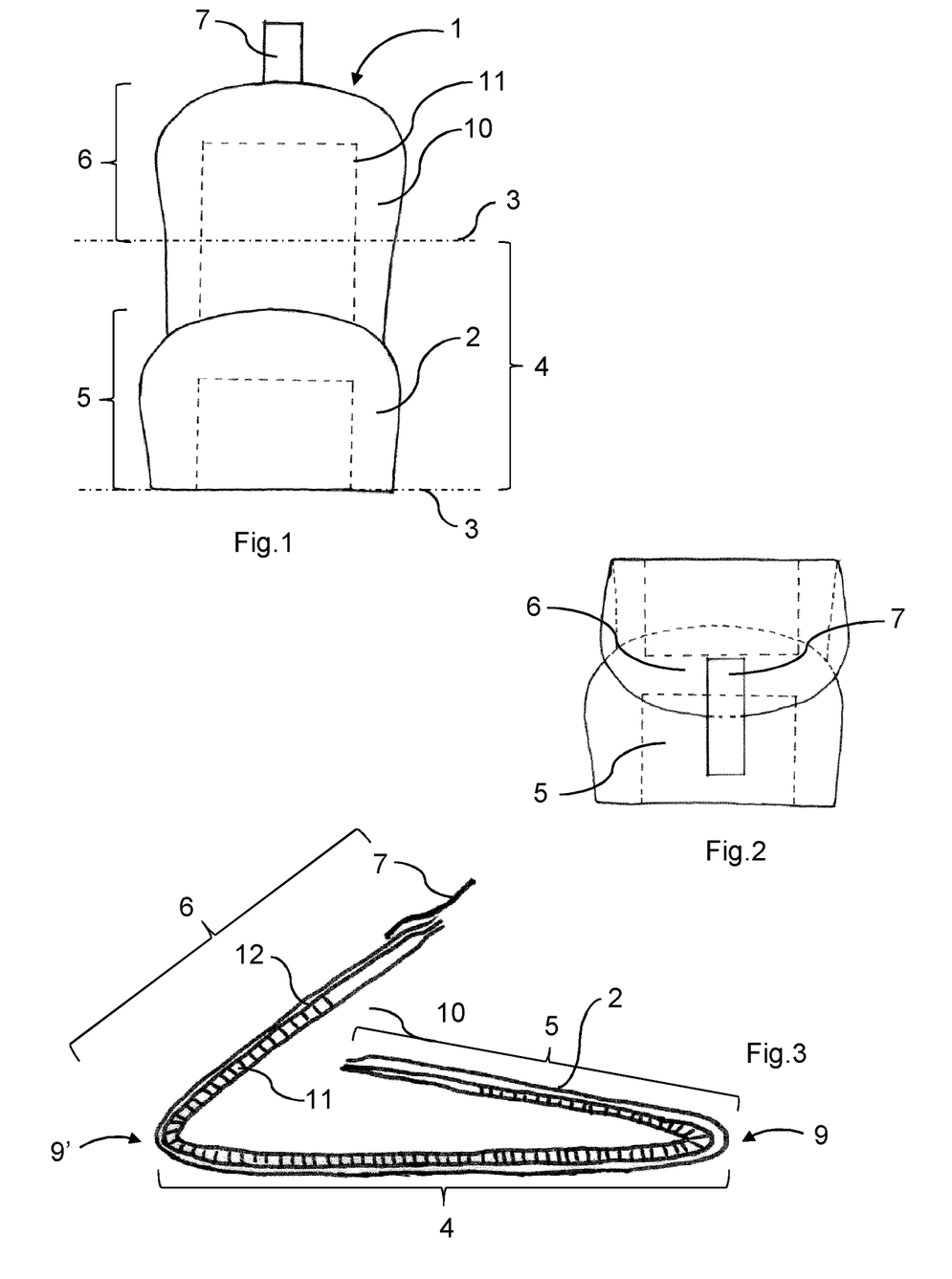
FIG. 1 is a schematic plan view of a pantyliner, in a semi-folded configuration.
FIG. 2 is a schematic plan view of the pantyliner of FIG. 1, in a tri-folded configuration.
FIG. 3 is a schematic side view of the pantyliner of FIG. 1, in a semi-folded configuration.

As illustrated in FIGS. 1 to 3, the absorbent article (1), including a topsheet (10), a backsheet (12) and an absorbent core (11), and the release paper (2), may advantageously be folded inwardly about two spaced-apart laterally oriented fold lines (3), thereby creating two folds fold (9, 9') in the article (1). As used herein, the "spaced-apart laterally oriented fold lines" refer to longitudinally offset lines, generally parallel the lateral direction, and about which the absorbent article (1) and release paper (2) are commonly folded. Folding the article about the two spaced-apart laterally oriented fold lines produces a folded arrangement defining three sections, a central section (4) and two outboard sections (5,6): one inner-outboard section (5) and one outer-outboard section (6). When folded, the inner-outboard section (5) is generally adjacent the central section (4), whilst the outer-outboard section (6) is relatively further from the central section (4) due to the interposition of the inner-outboard section (5). This configuration is generally called "tri-folded". The two outboard sections (5,6) may have a length, measured along the longitudinal centreline of the article, which is from 25 to 30% of the article's total length, measured along the longitudinal centreline of the article.

It may be advantageous, in such a tri-folded configuration, that there is no overlap of the absorbent core (11) of the article (1) in the two outboard sections (5,6), when these two overlap each other (as clearly visible in FIGS. 2 and 3). This may provide a folded article which has at most two superimposed layers of absorbent core (11—hatched zone in FIG. 3) (i.e. one layer in the central section (4) and another in either the inner-outboard section (5) or the outer-outboard section (6)), and thus a reduced and more constant thickness. This may have the additional advantage that there is no fold line within the functional zone of the absorbent core, which may result in a better fit and comfort for the user, and/or a reduced risk of leakage.

Optionally, the absorbent articles may comprise one or more wings on at least a portion of each of their longitudinal side edges. Each of said wings may comprise a second adhesive region on its garment facing side to adhere to a garment surface of the wearer. In this embodiment, the absorbent article comprises at least one protective strip over the second adhesive region to prevent it from adhering to the topsheet of the absorbent article when in its pre-use folded configuration.

The absorbent article for use according to the invention not being intended to be provided within an individual wrapping pouch, the applicant has found it was essential to provide each folded article with closure means for securing said folding, i.e. for maintaining the folded article in such folded configuration in a closed manner, avoiding that the outboard sections open, in particular before they are stacked and packed.

In a first embodiment the closure means comprise a closing tape (7) crossing and adhering in a resealable manner to the outer-outboard section (6) and to the inner-outboard section (5) of the tri-folded configuration. Advantageously it may be a strip of plastic film, for example PP or PE, or alternatively a strip of paper, similar to the release paper for example, partially or fully coated with an adhesive. Advantageously, a gripping end, free of adhesive, may enable the user to easily catch the closing tape. Such closing tape may have various shapes (e.g. rectangular, arrow); it may be partially transparent or opaque, coloured throughout the mass or by printing; it may be partially printed with different kinds of graphics, using one or more colours. It may comprise an indication to the user (e.g. a graphic indicating the orientation of the product when in use, a code to identify product size or type, an expiry date).

In a second embodiment the closure means comprise a portion of the release paper which is made longer than the absorbent article, said portion outlying at one end of the product, preferably at the end of the outer-outboard section of the tri-folded configuration. In an advantageous manner this outlying portion of the release paper is at least partially coated with an adhesive, to stick to another exposed surface of the release paper, preferably on the inner-outboard section of the tri-folded configuration. Advantageously, the outlying portion comprise a region free of adhesive where the user can grasp the release paper and easily remove it from the article.

In a third embodiment the closure means comprise a dot of glue which sticks together a region of the topsheet of the article and a region of the release paper, for example a region of the article's topsheet in the outer-outboard section of the tri-folded configuration and a region of the release paper on the inner-outboard section of the tri-folded configuration. In this embodiment, the glue is preferably selected to easily release from the topsheet material, whilst sticking better to the release paper, in order to avoid having glue residue on the body side of the absorbent article.

Figure 4:
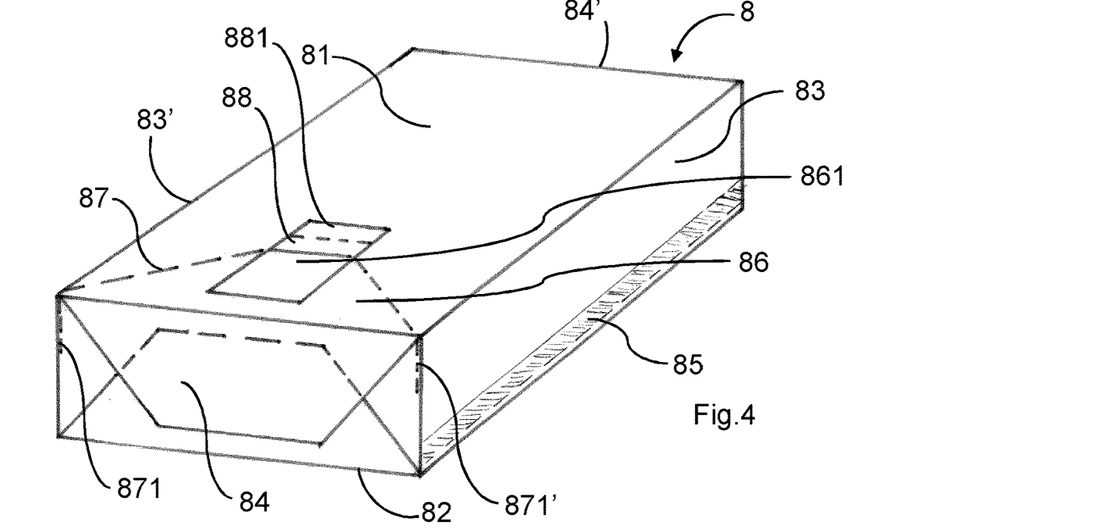
FIG. 4 is a schematic view of a package according to the invention.

The flexible package of the invention encloses at least 2 stacked folded articles, preferably at least 4, more preferably at least 6, still more preferably at least 8 stacked folded articles. It may include up to 30 articles, in particular with paper-thin products. It is reclosable, to have easy access to the absorbent articles and to keep them clean and hygienic. By "flexible package", we mean herein a container which, contrary to a carton box for example, is not hard or firm to the touch, but rather easy to compress or fold. It is also sometimes called "soft package". As it contains a stack of folded articles, it has a substantially cuboid outer shape, i.e. the outer shape of a solid which has six rectangular faces at right angles to each other. The package is said to be "substantially" cuboid, because since it is a flexible package, the angles may not be strictly at 90 degrees and the faces not strictly rectangular, but the overall impression of the package is still cuboid. The 6 faces of the package (8) of the invention, as in exemplary FIG. 4, are the front wall (81), the rear wall (82), two opposed side walls (83, 83') and two opposed end walls (84, 84').

The package is made of a wrapping material, wrapped around the stack of folded articles, and sealed at one position on either the front, the rear, or one of the two side walls, and on the two end walls. The wrapping material is advantageously a plastic film, selected from weldable or gluable plastic films, for example polyethylene or recyclable LDPE (which is flexible and not noisy). Preferred thicknesses for these films are in the range 20-50 µm, more preferably in the range 25-40 µm. Alternative wrapping materials are paper or a combination of paper and plastic, in particular a laminate of paper and plastic, for example paper laminated with a thin PE film of a few microns thickness. Preferably, as a first step, the wrapping material is wrapped around the stack of folded articles and sealed to form a tube around the articles. This sealing can be made by welding, e.g. thermal welding, for plastic wraps or paper-plastic laminates, or gluing for plastic, paper and paper-plastic laminated wraps. For plastic or plastic-containing wraps, welding is preferred, to avoid the extra use of an adhesive. This sealing (85) is preferably made longitudinally along the front, the rear, or one of the two side walls. Most preferably it is done in the region of an angle between the front wall or the rear wall and a side wall, or on a side wall itself, to keep the sealing as discreet as possible. Still preferably, as a second step, the still unsealed ends of the tube which project beyond the stack of articles are then folded over towards the contents of the pack and sealed, thereby forming the two end walls (84, 84') of the package (8). The end walls (84, 84') may be sealed by welding, e.g. thermal welding, for plastic wraps or paper-plastic laminates, or gluing for plastic, paper and paper-plastic laminated wraps. For plastic or plastic-containing wraps, welding is preferred, to avoid the extra use of an adhesive.

Figure 10:
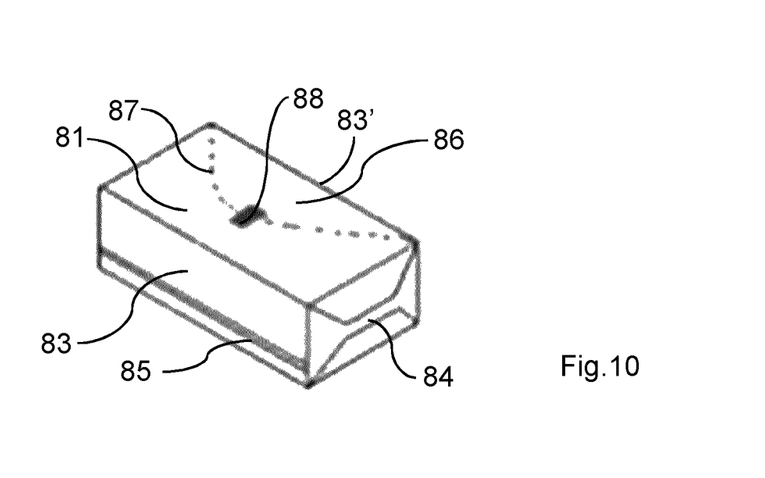
FIG. 10 is a schematic view of a package according to the invention.

The package further comprises, on at least one wall, a tear-open flap (86) limited by at least one tearing line (87). Such tearing line allows to tear an opening flap (or cap) wholly or partly off the remaining part of the package to expose the absorbent articles for removal. This provides a package which can be reliably opened and reclosed. The tearing line may be formed by any marking guaranteeing the tearability of the material, for example by a material weakening or by a full or partial cutting into the wrapping material, advantageously by adjoining perforations. In a preferred embodiment, the tear-open flap is provided in the front wall (81) or rear wall (82). Advantageously the front wall (or rear wall) is provided with a tear-open flap (86) which narrows to a grippable flap end (861) and which is limited by perforation lines (87) or by other markings guaranteeing the tearability of the material. Accordingly, in a package according to a preferred embodiment of the invention, there is formed in the region of one of the pack walls, especially in the upper region of the front wall (81), a tear-open flap (86) which is limited by tearing lines (87) favouring the tearing-open operation because of their arrangement. Said tearing lines may be arranged so that they diverge from the flap end (861), but at an angle to one another which is less than 180°. Differently shaped paths of the tearing lines are possible, for example trapezoidal, triangular or curved. In a most preferred embodiment of the invention, the tear-open flap is arranged in an end region of the front or rear wall in such a way that the tearing lines departing from the flap end towards the side walls run approximately up to vertical lateral edges and, indeed, in the upper corners of the package. Furthermore, the tearing lines preferably extend into the region of the end wall (871, 871'). In another embodiment, as in exemplary FIG. 10, the tear-open flap (86) is provided in the front wall (81), in a region along a side wall (83'), and the tearing line (87) is curved.

The package may also comprise a closing element (88) connected at its respective ends to adjacent wall portions of said package on opposite sides of the tearing line defining the tear-open flap. It may indeed be further provided that a closing element, preferably consisting of a paper or a film (e.g. HDPE or BOPP), is allocated to the tear-open flaps. This closing element may be fixed for a, preferably predominant, part to the tear-open flap, overlap the flap end and furthermore, be connected releasably to the adjoining part of the package. The connection of the closing element to the package may be ensured by means of adhesive, hook and loop fastener or pressure closing button, for example. Advantageously, the closing element is an adhesive strip. It may be provided with a gripping end (881) free of adhesive enabling the package to be opened by detaching the adhesive strip (88) from the package (8) and by pulling open the tear-open flap (86) by further pulling of the adhesive strip (88).

The wrapping material used to make the package may be fully or partially transparent or opaque, coloured throughout the mass or by printing. It may be partially printed with different kinds of graphics, using one or more colours. The closing element to open and close the package may have various shapes (e.g. rectangular, round, arrow, hart, flower); it may be fully or partially transparent or opaque, coloured throughout the mass or by printing; it may be partially printed with different kinds of graphics, using one or more colours.

Figure 9:
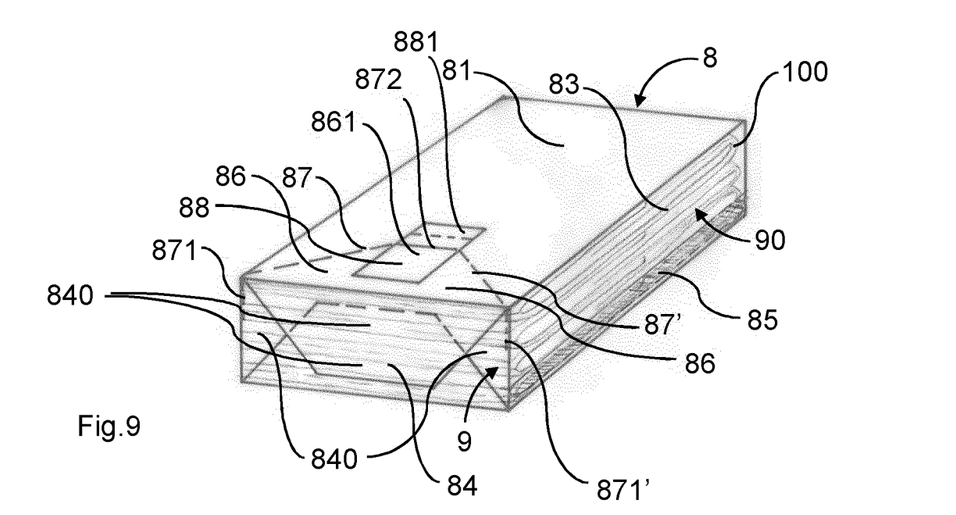
FIG. 9 is a schematic view of the package of the present example.

In an advantageous embodiment of the invention, the folded absorbent articles are appropriately so arranged that a fold (9, 9') faces the package opening formed by the tear-open flap (86) (as illustrated in FIG. 9, for example). This configuration may show two main advantages. The first is that it may become easier to grip the absorbent article for the purpose of removal: the folded edge of the article is straight and the article is stronger in the fold region. The second advantage mainly applies in the preferred configuration where the tear-open flap is arranged in a region close to an end wall. In that case the sealing of the end walls is done against a fold, i.e. against the release paper. This may have the advantage that the sealing step does not affect the integrity of the absorbent article, for example, in the case of thermal welding, it may limit the risk for the absorbent article suffering from the heat and for example partial melting.

In some embodiments of the invention, and in particular when the package is made of a plastic film, the package may further enclose an inner sheet of paper or carton, preferably between the plastic film and the absorbent articles. This may provide some additional rigidity to the assembly and/or provide indications to the consumer, such as manufacturer's name, trademarks, logos, indications for use, manual, graphics. The inner sheet may show up on 4, 3, 2 or 1 face(s) of the package. For example, the inner sheet may have a U-shape showing up on the side walls and the rear wall of the package, whilst the tear-open flap is present in an end region of the front wall.

Figure 11:
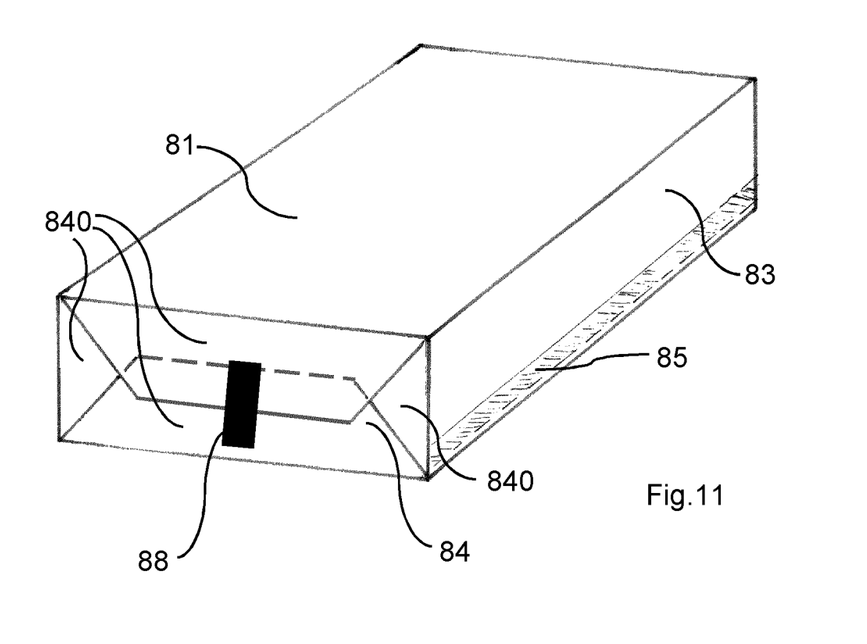
FIG. 11 is a schematic view of a package according to the invention.

In another aspect of the invention, the present disclosure relates to a process for making a substantially cuboid reclosable flexible package (8) of personal hygiene absorbent articles (1,100) free of an individual wrapping pouch, and a package made accordingly, having a front wall (81), a rear wall (82), two opposed side walls (83,83') and two opposed end walls (84,84'), as illustrated for example in FIG. 11. It comprises the steps of:
  (i) providing personal hygiene absorbent articles (1,100) comprising a garment attachment adhesive covered by a removable release paper (2);
  (ii) folding inwardly each individual absorbent article (1,100) into a folded article wherein the removable release paper (2) is exposed;
  (iii) providing each folded article with closure means (7) for securing said folding;
  (iv) stacking at least two folded articles;
  (v) delivering a continuous rectangular sheet of wrapping material;
  (vi) wrapping the sheet around the stack of folded articles;
  (vii) cutting the sheet longer than the periphery of the stack to create an overlap region (85),
  (viii) thereby forming a tube around the articles;
  (ix) folding over the open ends (840) of the tube towards the stack of articles;
  (x) sealing the sheet at least in two regions selected from the group consisting of the overlap region (85) and the two end walls (84,84');
  (xi) making one region selected from the group consisting of the overlap region (85) and the two end walls (84,84'), openable and reclosable.

According to this aspect of the invention, no tearing line needs to be provided in the wrapping material wrapping the stack of folded articles. On the other hand, the opening and reclosing of the package may be more complex and time consuming, since this operation needs the lifting and folding down of more than one flap (for example four flaps 840 in FIG. 11).

As apparent to the skilled man, most of the features described hereinabove in relation to the two first aspects of the invention also apply to this third aspect of the invention, apart from specific features relating to the tearing line, only present in the first aspects of the invention.

For example, in this aspect of the invention as well, the openable and reclosable region may be provided with a closing element (88) connected at its respective ends to adjacent openable portions of said package (8).

As another example, in this aspect of the invention as well, the folded absorbent articles are preferably arranged so that a fold (9) faces the openable and reclosable region.

According to the present aspect of the invention, the openable and reclosable region, may be sealed (either thermally or by adhesive) during the manufacturing process, in a way that it is easily openable, i.e. generally to a less degree than in the two other sealed regions which are not intended to be openable and reclosable.

These and additional features of the packages according to the invention, and of the processes of making such packages, will become apparent from the example explained in more detail below.

EXAMPLE

Figure 5:
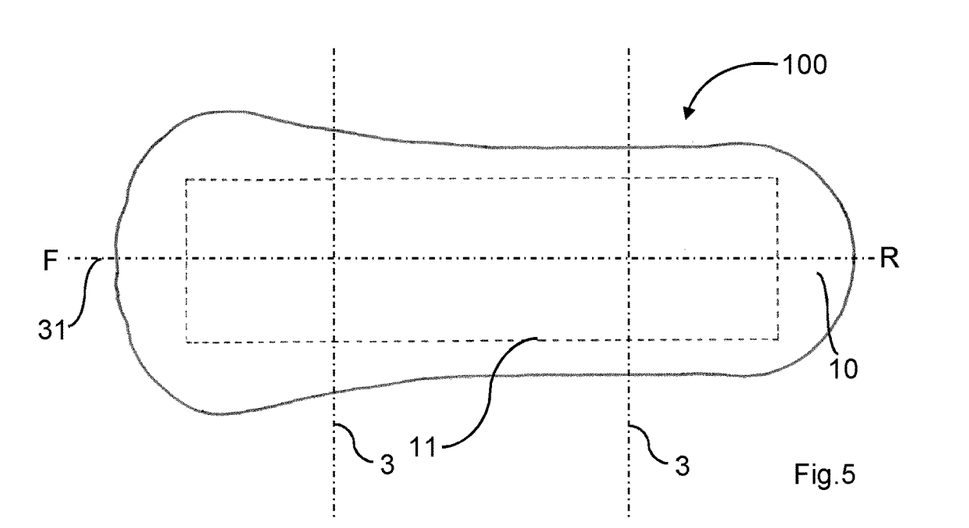
FIG. 5 is a schematic plan view of the asymmetrical pantyliner of the present example.
Figure 6:
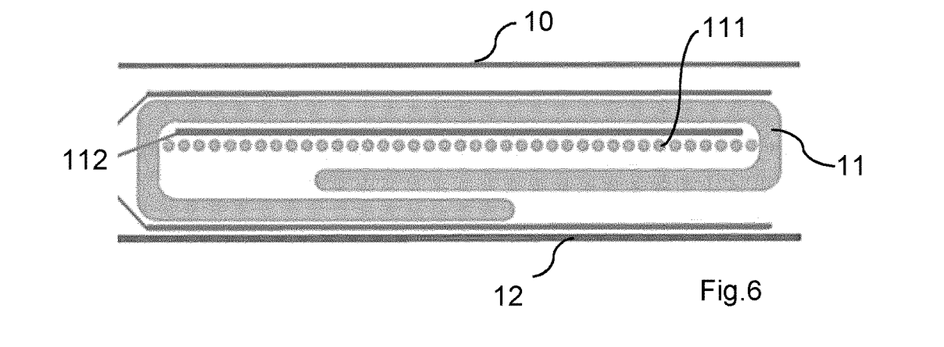
FIG. 6 is a schematic exploded transversal view of the pantyliner of the present example.

Pantyliners (100), as disclosed in FIGS. 5 and 6, are manufactured along a conventional manufacturing line, by assembling together in a conventional way a permeable topsheet (10), an impermeable backsheet (12), and, between the topsheet and the backsheet, a rectangular airlaid G-folded core (11) including super absorbent particles (111). All these elements are held in place by means of construction adhesive (112), and topsheet (10) and backsheet (12) are sealed together along the periphery of the pantyliner. The pantyliner (100) has a total length of 15 cm; the core (11) is 12 cm long and substantially centrally positioned in the pantyliner.

Such pantyliner construction is advantageously thin, thereby offering discretion, whilst offering sufficient absorption. The topsheet may be selected from premium raw materials, having for example premium look and feel, to provide softness to the face in contact with the body. Furthermore, embossing and/or printed graphics can be provided on the article to render the pantyliner even more attractive.

The backsheet is provided with five longitudinally oriented strips of garment attachment adhesive, one on the longitudinal centreline (31) of the absorbent article and two others on each side of the longitudinal centreline (31), and with a release paper which is siliconized on its face facing the garment attachment adhesive. For the purpose of this example a release paper of 36 gsm sold by Pasaco® under the reference Silcaform® 36 gsm was used.

Figure 7:
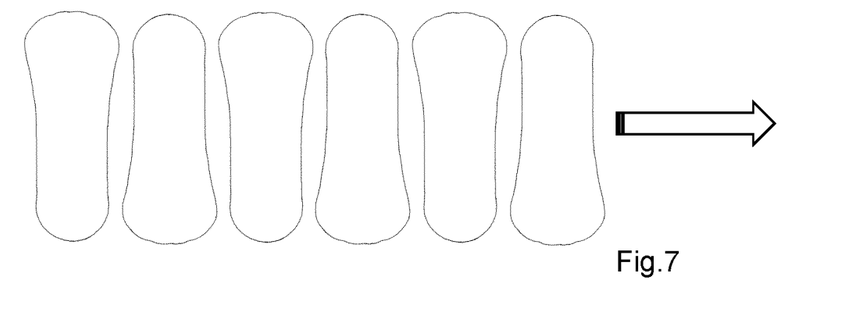
FIG. 7 is a schematic plan view of how the pantyliners of the present example are arranged along the manufacturing line.

The outer shape of the pantyliner is created by a die-cut operation through the whole stack of raw materials (from the topsheet to the release paper). The pantyliner is asymmetric between the front (F) and the rear (R) portions. This specific shape may offer a better "stay-in-place" when the product is in use, and/or offer increased discretion for daily comfort. In the present example, the asymmetrical pantyliners are cut in cross-machine direction, alternating in a "head-to-tail" manner, to use the raw materials in the most efficient way (see FIG. 7, wherein the arrow indicates the machine direction). Having the products on the line in a cross-machine direction also allows a significantly increased number of pantyliners being manufactured by minute.

Figures 8A, 8B:
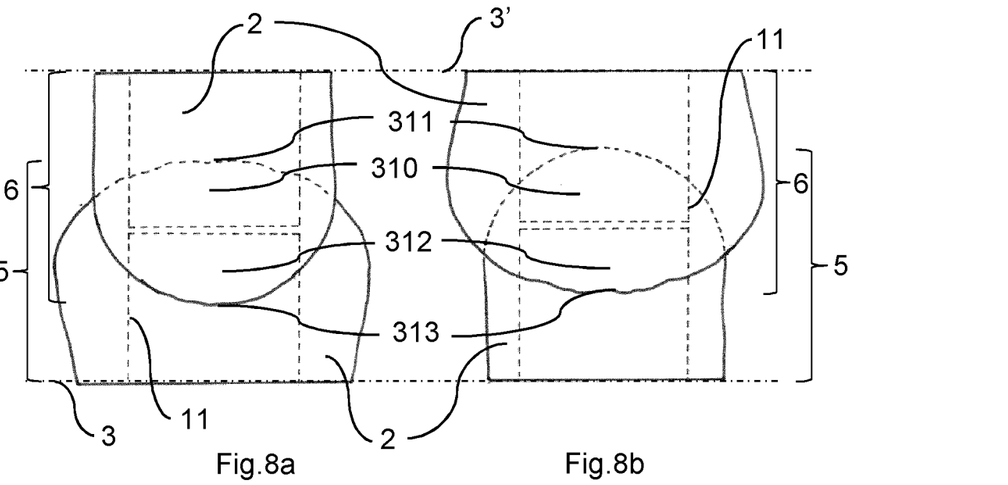
FIGS. 8*a* and 8*b* are schematic plan views of pantyliners of the present example, in folded configurations.

During their further progression on the manufacturing line (still in a cross-machine direction), the pantyliners are tri-folded, one after the other as illustrated in FIGS. 8a and 8b. One first end region (310) of the pantyliner (alternatively the front region (F) as in FIG. 8a and the rear region (R) as in FIG. 8b) is first folded along a first transversal folding line (3) distant from the first end edge (311) of the pantyliner by 4.5 cm, over the topsheet, so that the topsheet of the first end region (310) gets into contact with the topsheet of the central region of the pantyliner. This folded first end region corresponds to the inner-outboard section (5). Then the other end region (312) of the pantyliner (alternatively the rear region (R) as in FIG. 8a and the front region (F) as in FIG. 8b), the second end region (312), is folded along a second transversal folding line (3') distant from the second end edge (313) of the pantyliner by 4.5 cm, over the already folded first end region (310), so that the topsheet of the second end region (312) gets into contact partially with the topsheet of the central region of the pantyliner and partially with the release paper (2) of the first end region. This folded second end region corresponds to the outer-outboard section (6). The central region of the pantyliner, also called central section, is about 6 cm long. With such an arrangement, there is no overlap of the ends of the core (11) in the central region of the folded pantyliner; the folded pantyliner has at most two superimposed layers of absorbent core (i.e. one layer in the central section and another in either the inner-outboard section or the outer-outboard section), and thus a reduced and more constant thickness.

In a further step, a closing tape (not shown), crossing and adhering in a resealable manner to the outer-outboard section and to the inner-outboard section, is added. It is a rectangular piece of a 68 gsm polypropylene film, of about 2.8 cm long and 1 cm wide. It is coated with adhesive, except on one of its end, on the side of the inner-outboard section, to provide a gripping end to easily open the folded pantyliner before use.

The folded pantyliners are then stacked by 8 pieces, to provide a total package thickness of about 15 mm, which is practical to carry in a purse or in a pocket. They are stacked in an alternating "head-to-tail" manner, which leads to a regular overall cuboid shape, which is convenient for the following steps of the process, in particular for the packaging step, but also for the logistic behind (e.g. transportation in carton boxes) and also for the final package shape. The final package (8) is illustrated in FIG. 9 (where only 4 pantyliners (100) are drawn, for the clarity of the drawing).

A roll of transparent LDPE film from the company Gebrüder Dürrbeck Kunststoffe GmbH is delivering a continuous rectangular sheet of 30 μm thick LDPE, about 8 cm wide, which is wrapped around a stack of folded pantyliners (100), cut slightly longer than the periphery of the stack, to have some superposition of PE film, i.e. an overlap region (85), in a side wall (83) of the package (8) and then heat welded to form a tube around the pantyliners. The wrapping material around the pantyliners is covering the open sides (90) of the pantyliners, whilst the open ends of the tube face the folds (9) in the pantyliners. The end flaps (840) which project at the ends of the tube are then folded over towards the folded sides (9) of the pantyliners (100) and heat welded.

The rectangular front wall (81) of the package (8) is provided, in the upper region adjacent the upper end wall, with a tear-open flap (86). The tear-open flap is marked and limited by tearing lines (87, 87') which permit the tearing-open operation because of a material weakening in the original PE plastic film. The tear-open flap (86) shows a substantially trapezoidal shape by means of two perforation lines which run respectively to the corners of the front wall (81). A flap end (861) lying approximately centrally to the front wall (81) is marked here by a continuous parting cut (872) which joins to one another the adjacent ends of the perforation lines (87, 87'). This parting cut (872) facilitates the critical start of the tearing-open operation by gripping and pulling up the flap end (861). In order to provide by means of the tear-open flap (86) an opening which facilitates removal of the contents of the pack, the perforation lines (87, 87') are continued by adjoining perforations (871, 871') in the region of the end wall (84).

In a next step, an adhesive strip (88) is added to the tear-open flap (86). It is a rectangular piece of a 68 gsm polypropylene film, of about 2.8 cm long and 1.5 cm wide. This strip is connected by a longer sticking section to the tear-open flap (86) by adhesion. The adjoining pull-off part is made with a considerably smaller sticking area and is connected releasably by adhesion to the adjoining part of the front wall (81). A non-adhesive gripping end (881) formed at the end of the adhesive strip (88) enables the adhesive strip (88) to be gripped and pulled off. In so doing, with the package closed, the flap end (861) is first detached from the front wall (81). Upon a further pulling-off movement of the adhesive tape (88), the tear-open flap (86) is detached from the front wall (81) along the tearing lines (87,87',871,871'), since the adhesive strip (88) remains connected to the tear-open flap (86) because of corresponding adhesion. By means of this tearing-open operation there is exposed an opening which corresponds to the above-described tearing lines, and which enables the pantyliners to be removed one by one. After a partial removal the pack can be reclosed, namely by means of the adhesive strip (88). A repeated opening and closing operation can be performed.

Although the exemplary process of manufacturing has been hereinabove described with products made in cross-direction, the present invention can also be applied to products manufactured in machine direction. In this latter case, the products may have to go through a 90° turn device, before or after the folding step.

The invention was described by the hereinabove non-limiting examples which illustrate the invention, and are not intended to, nor should they be interpreted to, limit the scope of the invention. It is supposed that the present invention is not restricted to any form of realization described previously and that some modifications can be added to the presented example of fabrication without reappraisal of the appended claims.

The invention claimed is:

1. A process for making a substantially cuboid reclosable flexible package (8) of personal hygiene absorbent articles (1,100) free of an individual wrapping pouch, having a front wall (81), a rear wall (82), two opposed side walls (83,83') and two opposed end walls (84,84'), comprising the steps of:
(i) providing personal hygiene absorbent articles (1,100) comprising a garment attachment adhesive covered by a removable release paper (2), wherein each individual absorbent article (1,100) has a central section (4), an inner-outboard section (5) and an outer-outboard section (6), and wherein each individual absorbent article (1,100) is asymmetric between the outboard sections (5,6) and an outboard section extends laterally outward of the central section (4);

(ii) folding inwardly along two spaced-apart laterally oriented fold lines (3) the inner-outboard section (5) and the outer-outboard section (6) of each individual absorbent article (1,100) into a folded article wherein the removable release paper (2) is exposed;

(iii) providing each folded article with closure means (7) for securing the folded article;

(iv) stacking at least two folded articles;

(v) wrapping a wrapping material around the resulting stack of folded articles;

(vi) sealing the wrapping material at one position on either the front (81), the rear (82), or one of the two side walls (83,83'), and on the two end walls (84,84');

(vii) providing at least one wall of the package with a tear-open flap (86) limited by at least one tearing line (87).

2. The process according to claim 1, wherein a closing element (88) is further provided, which is connected at its respective ends to adjacent wall portions of said package (8) on opposite sides of said tearing line (87).

3. The process according to claim 1, wherein the personal hygiene absorbent articles (1,100) are provided by assembling a liquid impermeable backsheet (12), a liquid permeable topsheet (10) and an absorbent core (11) between the backsheet (12) and the topsheet (10), and the folding is done so that the folded articles have at most two superimposed layers of absorbent core (11).

4. The process according to claim 1, wherein the closure means (7) comprise a closing tape (7) crossing and adhering in a resealable manner to the outer-outboard section (6) and to the inner-outboard section (5).

5. The process according to claim 1, wherein the wrapping and sealing steps comprise:
(a) delivering a continuous rectangular sheet of wrapping material;
(b) wrapping the sheet around the stack of folded articles;
(c) cutting the sheet longer than the periphery of the stack to create an overlap region (85);
(d) sealing the sheet in the overlap region (85) to form a tube around the articles;
(e) folding over the open ends (840) of the tube towards the stack of articles;
(f) sealing said folded open ends.

6. The process according to claim 1, wherein the tear-open flap (86) is provided in an end region of the front (81) or rear (82) wall and narrows to a grippable flap end (861), and wherein two tearing lines depart (87,87') from the flap end (861) towards corners of the package (8) within said end region.

7. The process according to claim 6, wherein the tearing lines (871,871') extend into the region of the end wall (84).

8. The process according to claim 6, wherein a closing element (88) is adhered to the tear-open flap (86), overlaps the flap end (861) and is connected releasably to the front (81) or rear (82) wall.

9. The process according to claim 1, wherein the folded absorbent articles are arranged so that a fold (9) faces a package opening formed by the tear-open flap (86).

10. The process according to claim 1, wherein the absorbent articles (1,100) are progressing along the manufacturing line in cross-machine direction, at least during steps (i) and (ii).

11. The process according to claim 10, wherein the absorbent articles (1,100) are progressing along the manufacturing line in cross-machine direction, at least during steps (i), (ii), (iii) and (iv).

12. A substantially cuboid reclosable flexible package (8) of personal hygiene absorbent articles (1,100), having a front wall (81), a rear wall (82), two opposed side walls (83,83') and two opposed end walls (84,84'), wherein the package (8) includes a stack of at least two personal hygiene absorbent articles (1,100) comprising a garment attachment adhesive covered by a removable release paper (2), wherein each personal hygiene absorbent article (1,100) has a central section (4), an inner-outboard section (5) and an outer-outboard section (6), and wherein each personal hygiene individual absorbent article (1,100) is asymmetric between the outboard sections (5,6) and an outboard section extends laterally outward of the central section (4), and wherein the inner-outboard section (5) and the outer-outboard section (6) of each personal hygiene individual absorbent article (1,100) are folded inwardly along two spaced-apart laterally oriented fold lines (3) with the removable release paper (2) exposed, characterised in that the folded absorbent articles are free of an individual wrapping pouch and comprise closure means (7) for securing the folded absorbent articles and characterised in that the package (8) is made of a wrapping material sealed at one position on either the front (81), the rear (82), or one of the two side walls (83,83'), and on the two end walls (84,84'), and in that it comprises, on at least one wall, a tear-open flap (86) limited by at least one tearing line (87).

13. The package according to claim 12, characterised in that it comprises a closing element (88) connected at its respective ends to adjacent wall portions of said package (8) on opposite sides of said tearing line (87).

14. The package according to claim 12, wherein the folded absorbent articles are arranged so that a fold (9) faces a package opening formed by the tear-open flap (86).

15. A process for making a substantially cuboid reclosable flexible package (8) of personal hygiene absorbent articles (1,100) free of an individual wrapping pouch, having a front wall (81), a rear wall (82), two opposed side walls (83,83') and two opposed end walls (84,84'), comprising the steps of:
(i) providing personal hygiene absorbent articles (1,100) comprising a garment attachment adhesive covered by a removable release paper (2), wherein each individual absorbent article (1,100) has a central section (4), an inner-outboard section (5) and an outer-outboard section (6), and wherein each individual absorbent article (1,100) is asymmetric between the outboard sections (5,6) and an outboard section extends laterally outward of the central section (4);
(ii) folding inwardly along two spaced-apart laterally oriented fold lines (3) the inner-outboard section (5) and the outer-outboard section (6) of each individual absorbent article (1,100) into a folded article wherein the removable release paper (2) is exposed;
(iii) providing each folded article with closure means (7) for securing the folded article;
(iv) stacking at least two folded articles;
(v) delivering a continuous rectangular sheet of wrapping material;
(vi) wrapping the sheet around the stack of folded articles;
(vii) cutting the sheet longer than the periphery of the stack to create an overlap region (85),
(viii) thereby forming a tube around the articles;
(ix) folding over the open ends (840) of the tube towards the stack of articles;

(x) sealing the sheet at least in two regions selected from the group consisting of the overlap region (85) and the two end walls (84,84');

(xi) making one region selected from the group consisting of the overlap region (85) and the two end walls (84,84'), openable and reclosable.

16. The process according to claim 15, wherein the openable and reclosable region is further provided with a closing element (88) connected at its respective ends to adjacent openable portions of said package (8).

17. The process according to claim 15, wherein the folded absorbent articles are arranged so that a fold (9) faces the openable and reclosable region.

* * * * *